(12) United States Patent
Chambat et al.

(10) Patent No.: US 6,299,646 B1
(45) Date of Patent: Oct. 9, 2001

(54) KNEE PROSTHESIS WITH A ROTATIONAL PLATE

(75) Inventors: Pierre Chambat, Ste Foy les Lyon; Gérard Deschamps, Givry; Thierry Judet, Ville d'Avray; Philippe Neyret, Caluire, all of (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 09/158,791

(22) Filed: Sep. 23, 1998

(30) Foreign Application Priority Data

Sep. 23, 1997 (FR) .................................................. 97 12042

(51) Int. Cl.$^7$ ........................................................ A61F 2/38
(52) U.S. Cl. ........................................................ 623/20.33
(58) Field of Search .............................. 623/20.33, 20.29, 623/20.15

(56) References Cited

U.S. PATENT DOCUMENTS

| | | | |
|---|---|---|---|
| 4,714,474 | * 12/1987 | Brooks, Jr. et al. | 623/20.33 |
| 4,728,332 | 3/1988 | Albrektisson | 623/20 |
| 4,950,297 | * 8/1990 | Elloy et al. | 623/20.33 |
| 5,282,868 | 2/1994 | Bahler | 623/20 |
| 5,344,460 | * 9/1994 | Turanyi et al. | 623/20.33 |
| 5,658,342 | * 8/1997 | Draganich et al. | 623/20.33 |
| 5,683,468 | * 11/1997 | Pappas | 623/20.33 |
| 5,951,603 | * 10/1999 | O'Neil et al. | 623/20.33 |

FOREIGN PATENT DOCUMENTS

| | | |
|---|---|---|
| 0634156 | 1/1995 | (EP) . |
| 2707871 | 1/1995 | (FR) . |
| 2061730 | 5/1981 | (GB) . |

* cited by examiner

Primary Examiner—Bruce Snow
(74) Attorney, Agent, or Firm—Greenblum & Bernstein, P.L.C.

(57) ABSTRACT

Knee prosthesis comprising a metal base secured to an anchoring rod for fixing it into a tibia of a patient. A plastic tibia plate is freely slidable over the base. The metal base and the tibia plate are equipped with a guide mechanism defining a center of rotation offset from that of a tibia bone axis, so as to allow the plate to slide in rotation over the base. The guide mechanism is positioned a given distance from the center of rotation. The metal base comprises an upstand in the shape of an arc of a circle having a central part secured to lateral edges which are shorter than the central part. The tibia plate comprises, on a lower face thereof, a housing in the shape of an arc of a circle.

6 Claims, 11 Drawing Sheets

KNEE PROSTHESIS WITH A ROTATIONAL PLATE

BACKGROUND OF THE INVENTION

1. Field of the Invention

The present invention relates to a knee prosthesis and more specifically to the device for assembling its tibia plate, which is made of plastic, on its metal base anchored beforehand into the tibia bone tissue.

2. Discussion of Background Information

Knee prostheses which comprise a plastic tibia part which is free to rotate about the tibia bone axis with respect to the metal base secured to the tibia are known.

This freedom of rotation is generally achieved via a male shaft integral with the plastic tibia part which engages with a bore made in the metal base.

Furthermore, this freedom of rotation may be achieved by a male shaft secured to the metal base which engages with a bore made in the plastic tibia part.

These connecting devices have certain drawbacks, namely the difficulty of inserting the plastic tibia plate once the metal base is in place on the tibia. These drawbacks are exacerbated when the posterior cruciate ligament is being kept, as this restricts access to the upper part of the tibia.

Furthermore, it is observed that the center of rotation is necessarily positioned at a point of the device or [sic] the bore can be made, that is to say in a part or [sic] there is enough material to make the said bore. This arrangement of the center of rotation is not strictly anatomical.

It can be seen that the volume generated by the tibia bone axis may prevent a posterior cutout from being made in the plastic tibia plate or in the metal base to allow the posterior cruciate ligament to be kept.

Knee prostheses which comprise a plastic tibia plate which slides freely over the flat surface of the metal base, and the movement of which is limited by one or more cylindrical studs integral with the base communicating with spaces made in the plastic plate are also known.

This type of prosthesis has the drawback of not physically embodying an axis of rotation.

It is these drawbacks which the present invention sets out more particularly to overcome.

SUMMARY OF THE INVENTION

The knee prosthesis according to the present invention is intended to provide a plastic tibia plate which has a degree of freedom in rotation with respect to the metal base.

The knee prosthesis in accordance with the present invention comprises a metal base and a tibia plate which are equipped with guide mechanism defining a center of rotation which may be offset from that of the tibia bone axis, so as to allow the tibia plate to slide in rotation over the base, the guide mechanism being positioned a certain distance away from the center of rotation.

The knee prosthesis has guide mechanism which utilizes at least one upstand in the shape of an arc of a circle secured to the metal base and of a housing with the same radius of curvature made in the plastic tibia plate to allow the latter to slide in rotation about the center of rotation of the upstand.

The knee prosthesis according to the present invention comprises guide mechanism which utilizes an upstand in the shape of an arc of a circle, which upstand is positioned in the anterior part of the metal base and oriented in a substantially medio-lateral direction.

The knee prosthesis according to the present invention comprises additional guide mechanism which is positioned on or near to the center of rotation of the tibia plate on the metal base.

The knee prosthesis according to the present invention comprises additional guide means which are secured to a device making it possible to prevent the tibia plate from lifting from the metal base.

The knee prosthesis in accordance with the present invention comprises guide mechanism which utilizes at least two pegs set out in an arc of a circle and defining a center of rotation, and of a housing of the same radius of curvature formed in the tibia plate.

The knee prosthesis according to the present invention comprises a metal base which comprises an upstand in the shape of an arc of a circle having a central part secured to lateral edges which are not as tall as the said central part, while the tibia plate comprises, on its lower face, a housing in the shape of an arc of a circle.

The knee prosthesis according to the present invention comprises an upstand which has a center of rotation which is borne by the tibia bone vertical axis, while the upstand is a certain distance away from its center of rotation.

The knee prosthesis according to the present invention comprises an upstand which has a center of rotation which is offset from the tibia bone vertical axis, while the upstand is a certain distance away from its center of rotation.

The knee prosthesis according to the present invention comprises a metal base which has two upstands in the shape of an arc of a circle, of constant height and having one and the same center of rotation, while the tibia plate comprises two housings in the shape of an arc of a circle.

The knee prosthesis according to the present invention comprises upstands which are set out opposite one another, and have one and the same center of rotation.

The knee prosthesis according to the present invention comprises a metal base which has, opposite the upstand, a retaining peg borne by a center of rotation so as to engage with a cutout formed in the tibia plate to prevent the latter from lifting off the base as the plate slides in rotation about its center of rotation.

The knee prosthesis according to the present invention comprises a retaining peg which utilizes a cylindrical pin integral with a head which has a larger diameter than the pin so that the head engages with inclined faces made in the cutout.

The knee prosthesis according to the present invention comprises a metal base which has, opposite the upstand, a centering peg borne by the center of rotation so as to engage with a blind hole formed in the tibia plate to guide the latter with respect to the base as the plate slides in rotation about its center of rotation.

The knee prosthesis according to the present invention comprises a metal base and a tibia plate which respectively comprise a cutout through which the posterior cruciate ligament can pass.

The knee prosthesis according to the present invention comprises a metal base which has two upstands in the shape of an arc of a circle curved in the same direction and centered about the same center of rotation, while the tibia plate comprises housings intended to receive the upstands respectively, so as to allow the plate to slide in rotation about the center of rotation.

The knee prosthesis according to the present invention comprises an upstand which is integral with a flange which engages in a slot in the housing to prevent the tibia plate from lifting off the metal base as the plate slides in rotation about the center of rotation.

The knee prosthesis according to the present invention comprises a metal base which comprises two upstands in the shape of an arc of a circle in opposite directions and centered about the same center of rotation, while the tibia plate comprises an element and a housing which are intended to receive the upstands respectively to allow the plate to slide in rotation about the center of rotation.

The knee prosthesis according to the present invention comprises an upstand which is set out on the external periphery of the horizontal disk of the metal base so as to engage with a peripheral recess in the tibia plate.

The knee prosthesis according to the present invention comprises an upstand which is offset from the center of rotation and comprises a flange which snap-fastens into the housing in the tibia plate to, on the one hand, guide the plate as it slides in rotation about its center and, on the other hand, retain the plate so that it does not lift off the metal base.

The knee prosthesis according to the present invention comprises a metal base which comprises a peripheral upstand in the shape of an arc of a circle integral with a flange directed toward the tibia bone vertical axis and a housing set out in the region of the center of rotation, while the tibia plate has, on its external periphery, a recess in which there is formed a horizontal slot intended to receive the flange of the upstand and, on its lower face, a stub which engages with the housing.

The knee prosthesis according to the present invention comprises a metal base which comprises three peripheral upstands extending vertically above the horizontal disk, while the tibia plate has, on its external periphery, three recesses intended to receive the upstands respectively to allow the plate to be guided as it slides in rotation about the center of rotation.

The knee prosthesis according to the present invention comprises pegs which are set out in an arc of a circle about a center of rotation, while the tibia plate has a housing intended to receive the pegs.

The knee prosthesis according to the present invention comprises pegs which have a center of rotation which is borne by the tibia bone vertical axis, while the peg is a certain distance away from its center of rotation.

The knee prosthesis according to the present invention comprises pegs which have a center of rotation which is offset from the tibia bone vertical axis, while the peg is a certain distance away from its center of rotation.

The knee prosthesis according to the present invention comprises a metal base which comprises at least one upstand or peg which engages with a housing of the tibia plate so that the plate can slide in rotation over the metal base only within the limit set by the difference in size between the upstand or peg and the corresponding housing.

The knee prosthesis according to the present invention has a rotational travel between the tibia plate and the metal base which is reduced to zero when the dimensions of the housing are made so as to engage without clearance with the upstand.

The knee prosthesis according to the present invention has a short height of the guide mechanism and of their anterior positioning on the metal base which allows the tibia plate to be mounted on the base via a strictly anterior approach, the plate requiring upward clearance only by the height of the guide mechanism.

BRIEF DESCRIPTION OF THE DRAWINGS

The description which will follow with reference to the appended drawings, given by way of nonlimiting examples, will allow a good understanding of the invention, its features and the advantages it is likely to afford.

DETAILED DESCRIPTION OF THE PRESENT INVENTION

Figure 1:
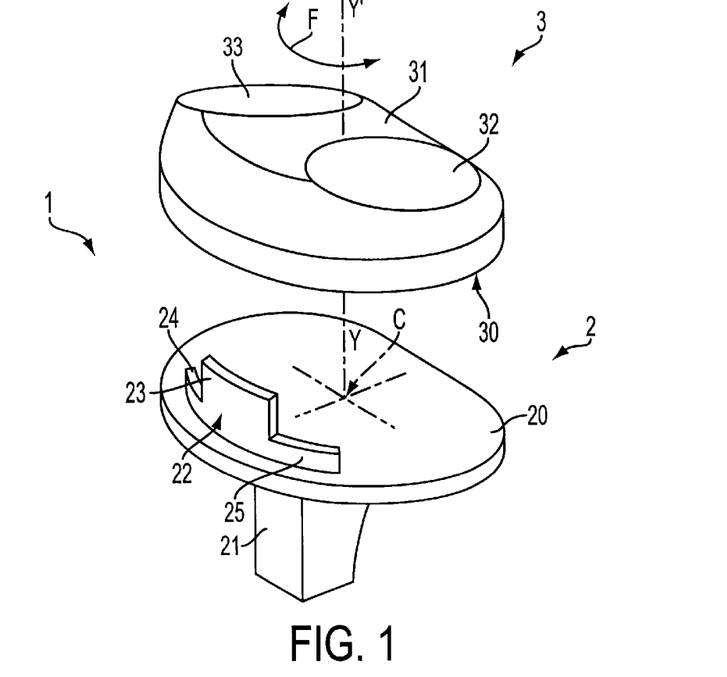
FIG. 1 is an exploded perspective view illustrating the knee prosthesis according to the present invention.
Figure 2:
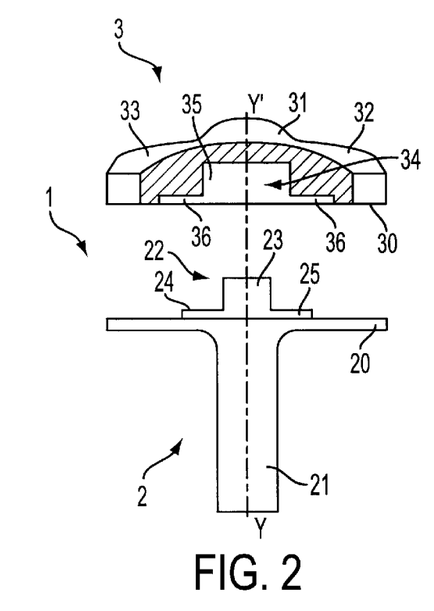
FIGS. 2 and 3 are side views showing the knee prosthesis before the plastic tibia plate is fitted on the metal base.
Figure 3:
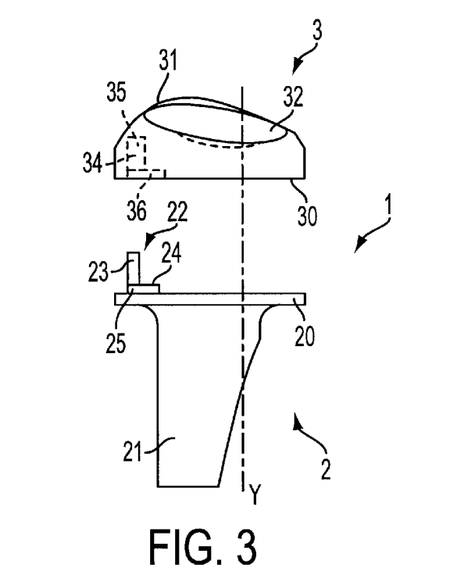

FIGS. 1 to 3 show a knee prosthesis 1 comprising a metal base 2 and a tibia plate 3, whereas the femoral element is not depicted.

The metal base 2 consists of a horizontal disk 20 secured on one of its faces to an anchoring rod 21 allowing the base 2 to be fixed into the tibia of a patient.

The horizontal disk 20 comprises, on the opposite side to the rod 21, a guide mechanism which utilizes an upstand 22 with an exterior profile in the shape of an arc of a circle. In this case, note that the center of rotation C of the upstand 22 is borne by the tibia bone vertical axis YY'.

The upstand 22 extending vertically above the horizontal disk 20 has a central part 23 integral on each side with two vertical edges 24 and 25 which are not as tall as the central part 23.

In addition, the upstand 22 is positioned on the horizontal disk 20 of the metal base 2 a certain distance away from the center of rotation C.

The tibia plate 3, which is made of plastic, has a flat lower face 30 arranged in a horizontal plane parallel to the plane containing the disk 20 of the metal base 2.

On the opposite side to the face 30 the tibia plate 3 has an upper face 31 with two tracks 32 and 33 of concave profile which are intended to receive the condyles of the femoral element, not depicted.

The lower face 30 is pierced with a housing 34 with the same radius of curvature as the upstand 22 secured to the metal plate 2.

The housing 34 has cutaways 35 and 36 of a larger size which are intended to receive respectively the central part 23 and the lateral edges 24 and 25 of the upstand 22.

It can be seen that the tibia plate 3, and more particularly its lower face 30, is resting on the horizontal disk 20 of the metal base 2, that the upstand 22 enters the housing 34.

The latter has dimensions that exceed those of the upstand 22 so that the tibia plate 3 can slide freely in rotation about the center of rotation C of the upstand 22 in the direction of the arrow F illustrated in FIG. 1.

The upstand 22, which is in the shape of an arc of a circle or curved, is positioned in the anterior part of the metal base 2 and oriented in a substantially medio-lateral direction.

Figure 4:
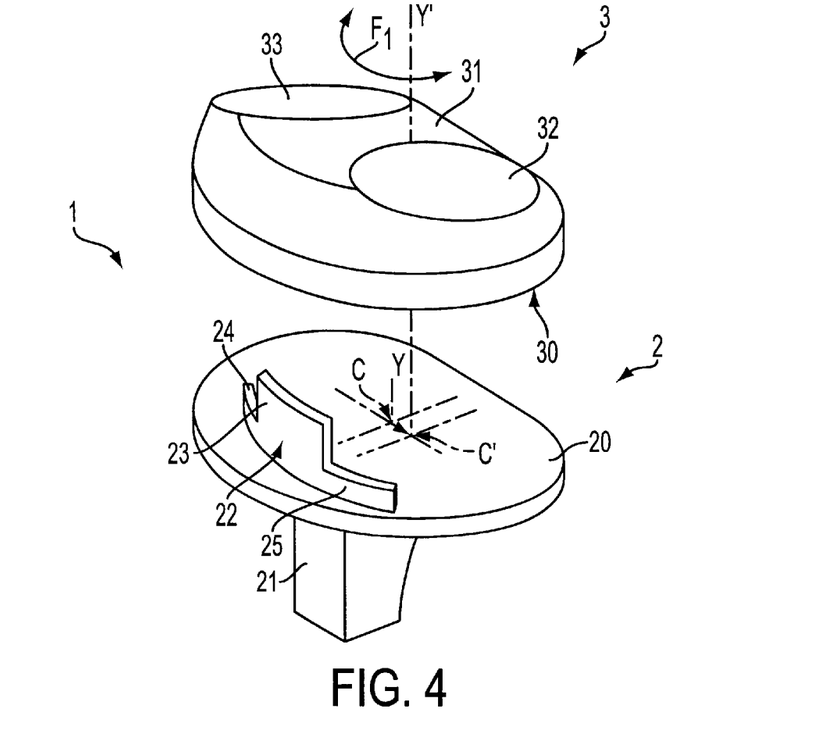
FIGS. 4 and 5 are views depicting a first alternative form of the knee prosthesis according to the invention.
Figure 5:
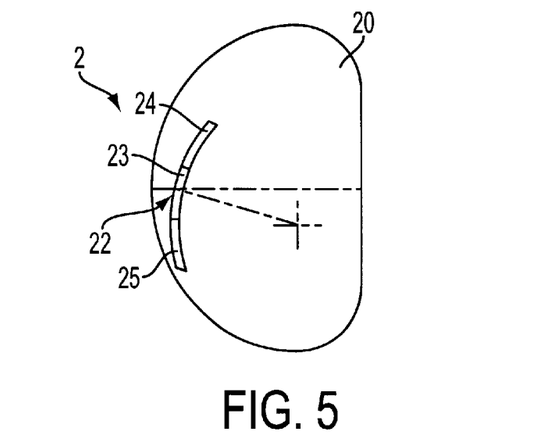

FIGS. 4 and 5 show a first alternative form of the knee prosthesis 1 according to the present invention.

The knee prosthesis 1 is identical to the one described earlier, that is to say that it comprises a metal base 2 and a plastic tibia plate 3.

The metal base 2 has, and this is what differentiates it from the one described above, the position of the guide mechanism on the horizontal disk 20. In effect, the guide mechanism utilizes an upstand 22 in the shape of an arc of a circle and the profile of which is similar to the one described earlier, but the center of rotation C' of which is offset from that C borne by the tibia bone vertical axis YY'.

Note that the center of rotation C' can be positioned anywhere, either on the horizontal disk 20 or off it, while at the same time keeping the guide mechanism on the horizontal disk 20 and more specifically at a particular point.

Just as before, the upstand 22 provided with its central part 23 and its lateral edges 24 and 25 enters the housing 34 formed in the lower face 30 of the plastic tibia plate 3 to allow the latter to slide in rotation over the metal base 2 and about the center of rotation C' in the direction of the arrow F1 in FIG. 4.

The upstand 22, which is in the shape of an arc of a circle or curved, is positioned in the anterior part of the metal base 2 and oriented in a substantially medio-lateral direction.

Figure 6:
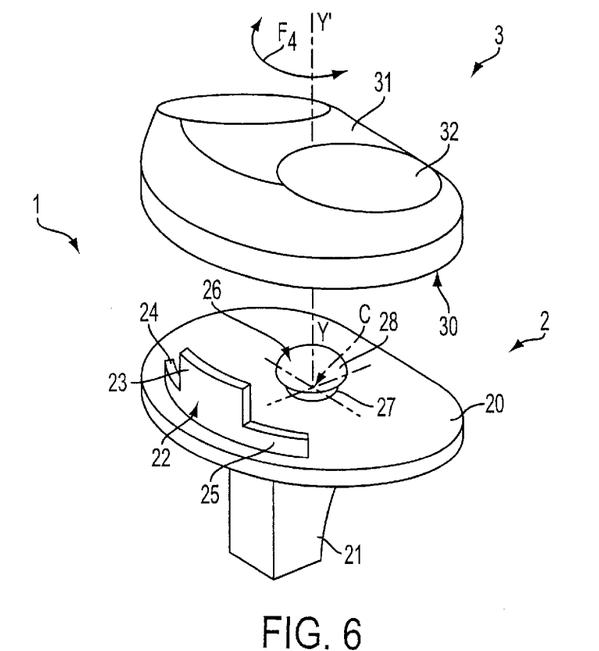
FIGS. 6, 7 and 8 are views showing a second alternative form of the knee prosthesis in which the metal base has, on its axis of rotation, a peg for retaining the plastic tibia plate.
Figure 7:
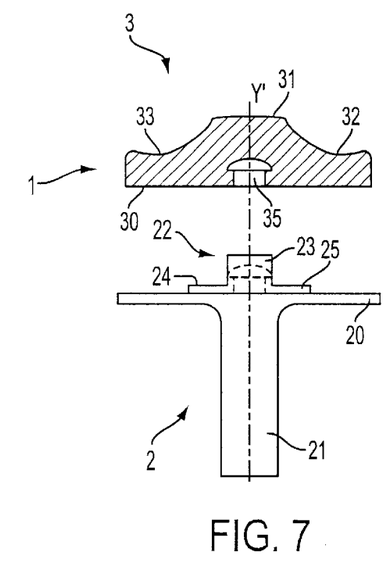
Figure 8:
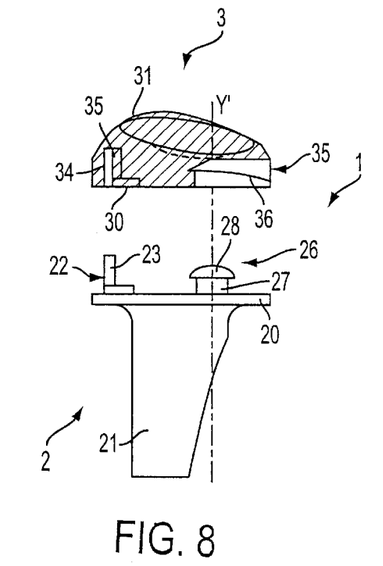

FIGS. 6 to 8 illustrate a second alternative form of the knee prosthesis 1 according to the present invention.

The knee prosthesis 1 is identical to the one described in FIGS. 1 to 3, namely it comprises a metal base 2 and a plastic tibia plate 3.

The metal base 2 comprises, on its horizontal disk 20, and on the opposite side to its anchoring rod 21, guide mechanism which utilizes the upstand 22 formed from a central part 23 and of two lateral edges 24 and 25.

Furthermore, the horizontal disk 20 comprises, at the center of rotation C of the upstand 22 which is borne by the tibia bone vertical axis YY', a retaining peg 26 extending vertically above the said disk 20.

The retaining peg 26 constitutes a guide means that is in addition to the guide means formed by the upstand 22. Thus, the peg 26 is positioned on the center of rotation C of the tibia plate 3 on the metal base 2.

The retaining peg 26 consists of a cylindrical pin 27 integral with a head 28 whose outside diameter exceeds that of the pin.

The additional guide mechanism or peg 26 is an integral part of the pin 27, 28 to prevent the tibia plate 3 from lifting off the metal base 2 when the prosthesis is in motion.

The tibia plate 3 has, on its lower face 30, the housing 34 that receives the upstand 22 and a cutout 35 with inclined faces 36. When the plate 3 is mounted on the base 2, this cutout engages with the retaining peg 26 so that the head 28 lies above the inclined faces 36.

It can be seen that the retaining peg 26, when it engages with the cutout 35, allows the tibia plate 3 to be prevented from lifting under a tensile force when the plate is sliding in rotation F4 on the metal base 2.

Figure 9:
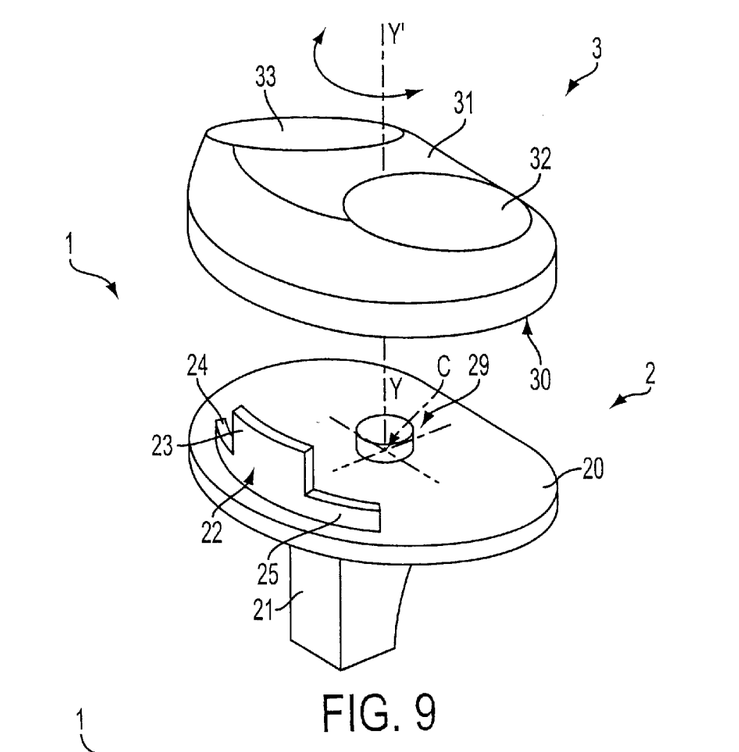
FIGS. 9, 10 and 11 are views showing a third alternative form of the knee prosthesis in which the metal base has, on its axis of rotation, an additional peg for centering the plastic tibia plate.
Figure 10:
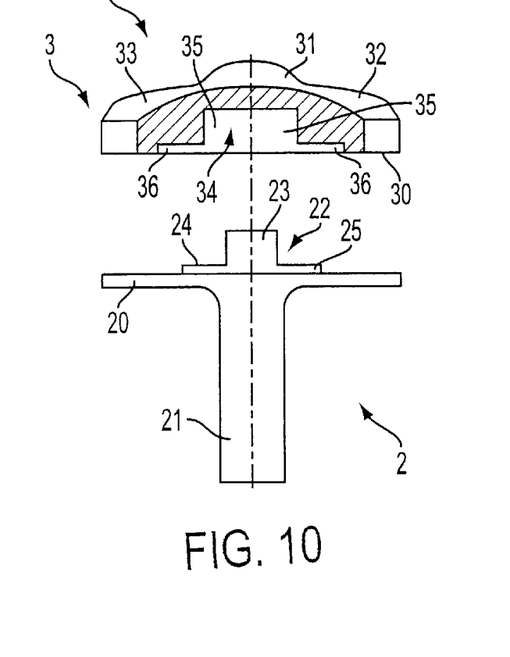
Figure 11:
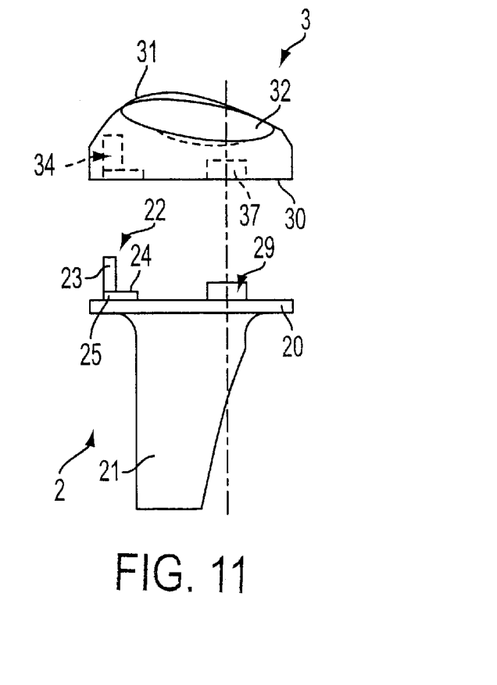

FIGS. 9 to 11 show a third alternative form of the knee prosthesis 1 according to the invention.

Thus, the metal base 2 comprises, opposite the upstand 22, and in the region of the center of rotation C which is borne by the tibia bone vertical axis YY', a centering peg 29 extending vertically above the horizontal disk 20.

The centering peg 29 extends vertically above the horizontal disk 20 by a short height, constituting a guide mechanism that is in addition to the guide mechanism formed by the upstand 22.

The centering peg 29 consists of a short cylindrical pin.

The plastic tibia plate 3 comprises, on its lower face 30 and opposite the housing 34, a blind hole 37 intended to receive the centering peg 29 when the plate is fitted onto the metal base 2.

The centering peg 29 provides a physical embodiment of the center of rotation C of the upstand 22 as the tibia plate 3 slides in rotation over the metal base 2.

Figure 12:
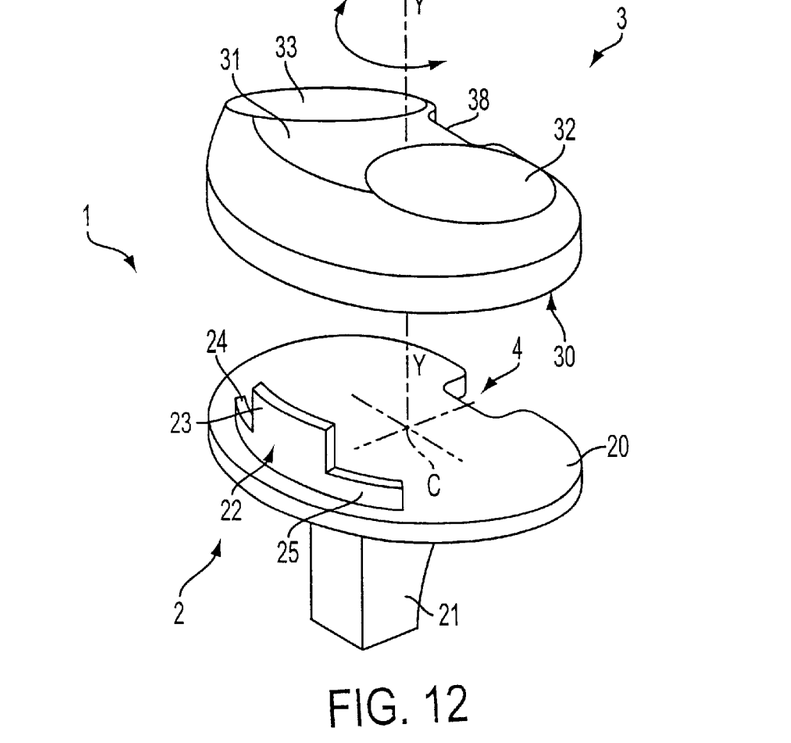
FIGS. 12, 13 and 14 are views depicting a fifth alternative form of the knee prosthesis which has a cutout through which the posterior cruciate ligament can pass.
Figure 13:
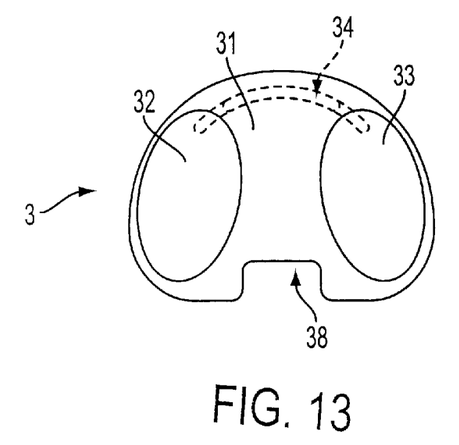
Figure 14:
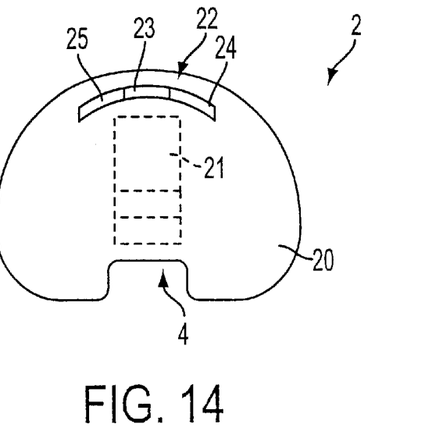

The knee prosthesis 1 illustrated in FIGS. 12 to 14 differs from the one shown in FIGS. 1 to 3 only in the fact that the metal base 2 and the plastic tibia plate 3 respectively comprise a cutout 4 and 38 for the passage of the posterior cruciate ligament.

Quite obviously, the prosthesis 1 shown in FIGS. 12 to 14 works in the same way as the one described in FIGS. 1 to 3.

Figure 15:
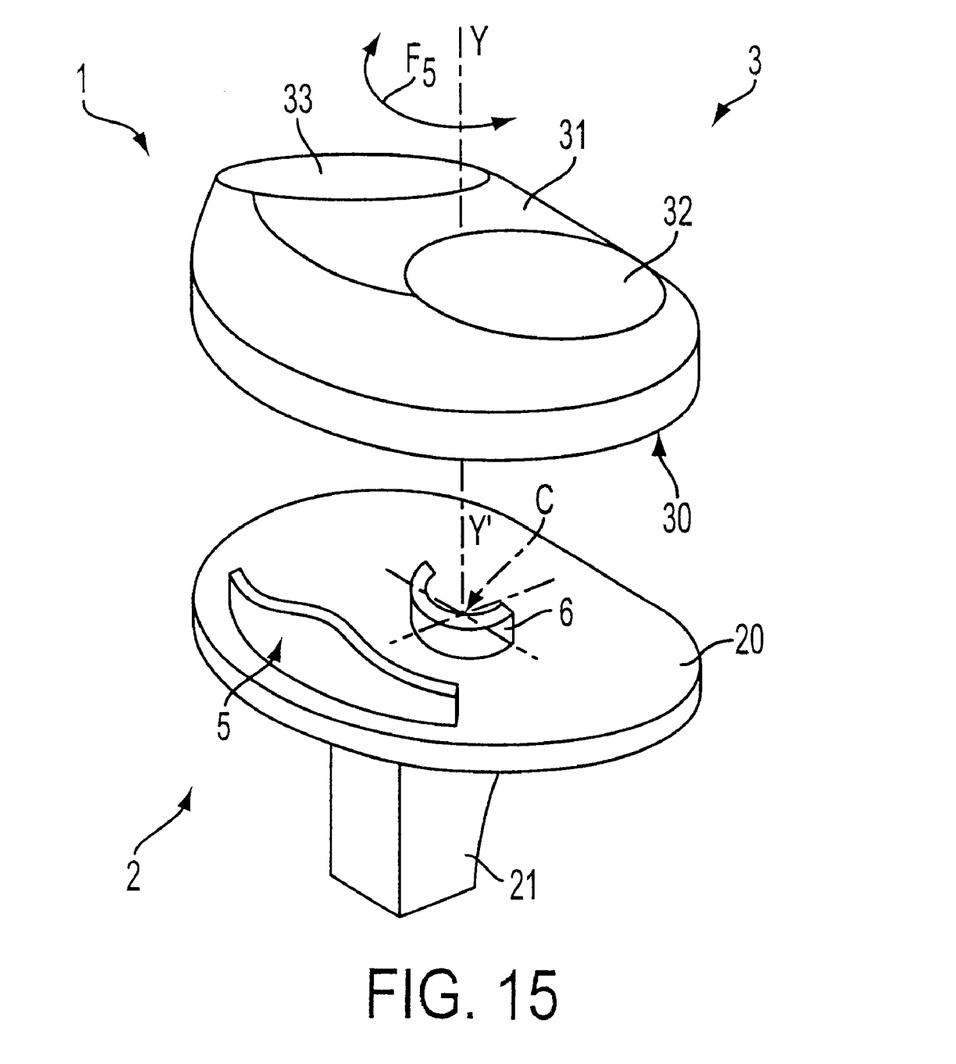
FIGS. 15 to 21 are views illustrating alternative forms of the knee prosthesis in which the metal base has two opposed guide upstands but one of which is borne by the center of rotation of the second.

FIG. 15 shows the knee prosthesis 1 equipped with its metal base 2 and with its tibia plate 3. The metal base 2 comprises, on its horizontal disk 20, and more specifically on the opposite side to the anchoring rod 21, an upstand 5 in the shape of an arc of a circle and of variable height. This upstand has a profile which differs from those that make up the upstands described earlier. At the center of rotation C of the upstand 5 there is a second upstand 6 in the shape of an arc of a circle.

The upstands 5 and 6 engage in housings, not depicted, but formed on the face 30 of the tibia plate 3 to allow the plate to be guided as it slides in rotation about the center of rotation C, as depicted by the arrow F5.

The upstand 5, in the shape of an arc of a circle or curved, is positioned in the anterior part of the metal base 2 and oriented in a substantially medio-lateral direction.

The upstand 6 constitutes a guide mechanism that is in addition to the guide mechanism formed by the upstand 5.

Thus, the upstand 6 is positioned on the center of rotation C of the tibia plate 3 on the metal base 2.

Provision may be made for the center of rotation of the upstands 5 and 6 to be offset from the tibia bone vertical axis YY' without this in any way altering the subject of the invention.

Figure 16:
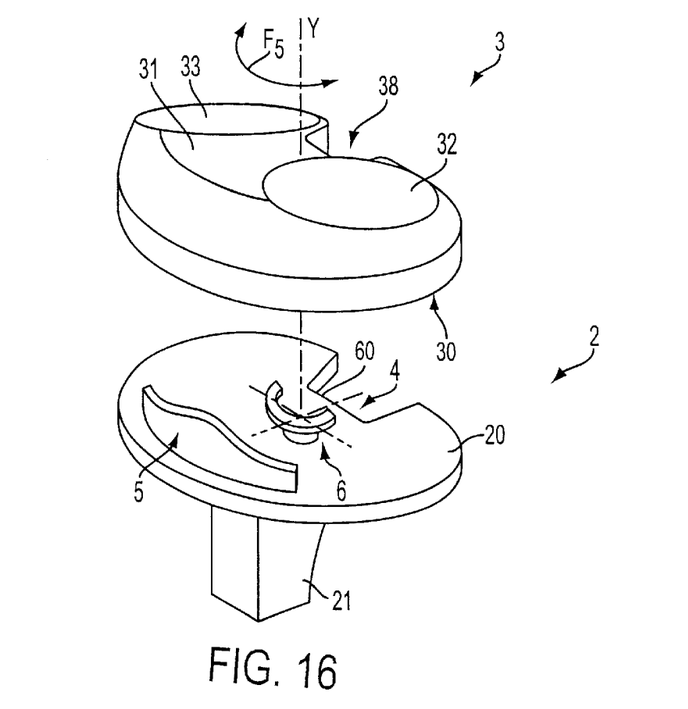
Figure 17:
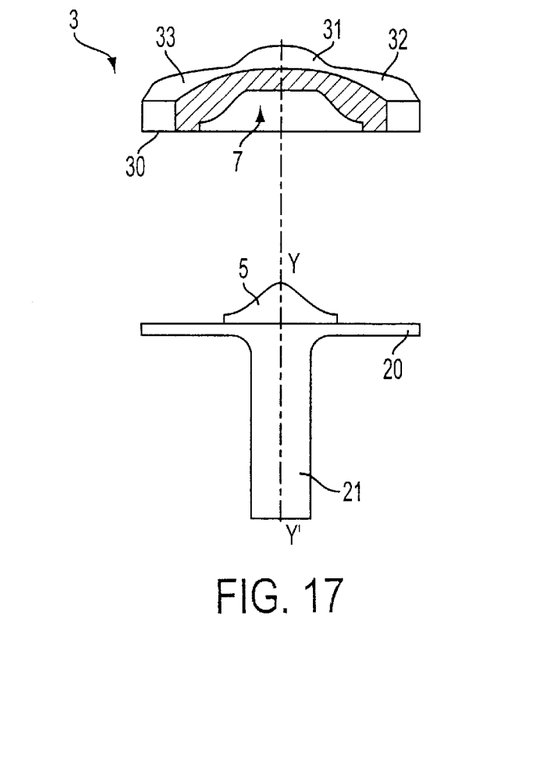
Figure 18:
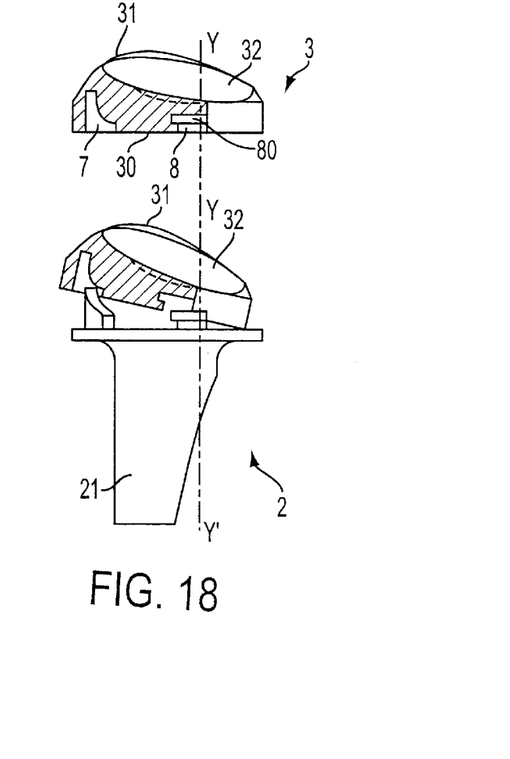

FIGS. 16 to 18 depict an alternative form of the knee prosthesis 1 shown in FIG. 15, namely wherein the upstand 6 is integral with a flange 60 forming a kind of small plate set out in a horizontal plane parallel to the plane containing the disk 20 of the metal base 2.

The tibia plate 3 has, on its face 30, housings 7 and 8 intended to receive respectively the upstands 5 and 6 to allow the tibia plate 3 to slide in rotation over the metal base 2 about the center of rotation C and in the direction of the arrow F5.

The housing 7 has a profile essentially identical to that of the upstand 5, and at the very least, in the shape of an arc of a circle for guiding the tibia plate 3 in its travel.

The housing 8 has a profile essentially identical to the flange 60 of the additional guide mechanism or upstand 6 for guiding the tibia plate 3 in its travel.

The housing 8 is pierced with an internal slot 80 intended to receive the flange 60 of the upstand 6 to achieve a kind of snap-fastening of the tibia plate 3 to the base 2, so that the plate cannot lift under a tensile force.

Note that the upstands 5 and 6 in the shape of an arc of a circle are curved in the same direction and about the same center of rotation C or C' when the latter is offset from the tibia bone vertical axis YY'.

As in FIG. 12, the metal base 2 and the tibia plate 3 may respectively comprise cutouts 4 and 38 for the passage of the posterior cruciate ligament.

Figure 19:
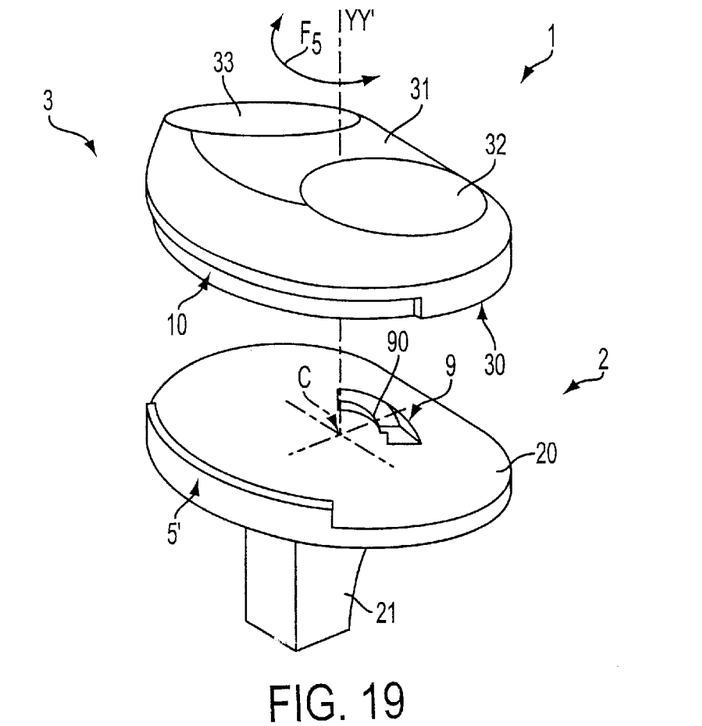
Figure 20:
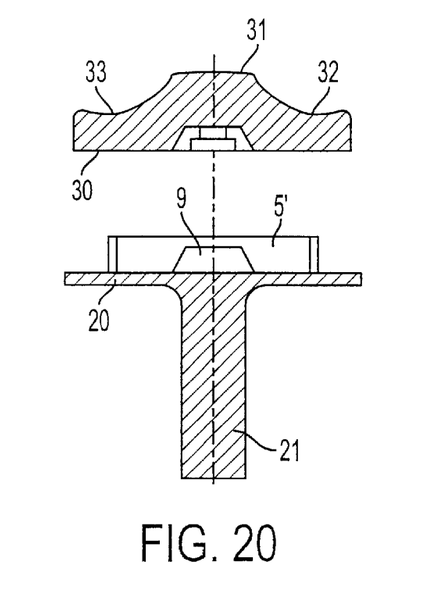
Figure 21:
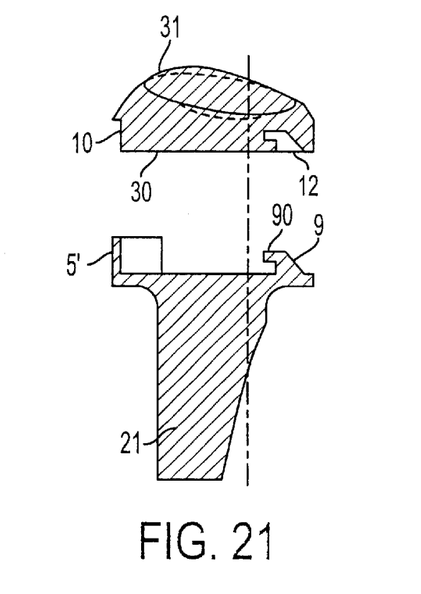

In FIGS. 19 to 21 the knee prosthesis 1 comprises, on its metal base 2, a first upstand 5' set out at the external periphery of the horizontal disk 20. Opposite the upstand 5' the horizontal disk 20 is secured to another upstand 9 in the shape of an arc of a circle, but the radius of curvature of which is inverted compared with that of the upstand 5'.

The upstand 5, which is in the shape of an arc of a circle or curved, is positioned in the anterior part of the metal base 2 and oriented in a substantially medio-lateral direction.

The upstand 9 constitutes a guide mechanism that is in addition to the guide mechanism formed by the upstand 5'. Thus, the upstand 9 is positioned on the center of rotation C of the tibia plate 3 on the metal base 2.

The upstand 9 has the same center of rotation C as the upstand 5', but the center may be offset, depending on the configuration of the knee prosthesis, from the tibia bone vertical axis YY'.

The upstand 9 is integral with a flange 90, the function of which will be seen more clearly later.

The tibia plate 3 has, on its lower periphery, that is to say the one that lies between the faces 30 and 31, a recess 10 receiving the upstand 5' when the tibia plate 3 is fitted onto the metal base 2.

On the opposite side to the recess 10, the lower face 30 is pierced with a housing 12 into which the upstand 9 can be snap-fastened to, on the one hand, guide the plate 3 as it slides in rotation about its center C, and, on the other hand, retain the plate to prevent it from lifting off the metal base 2.

Figure 22:
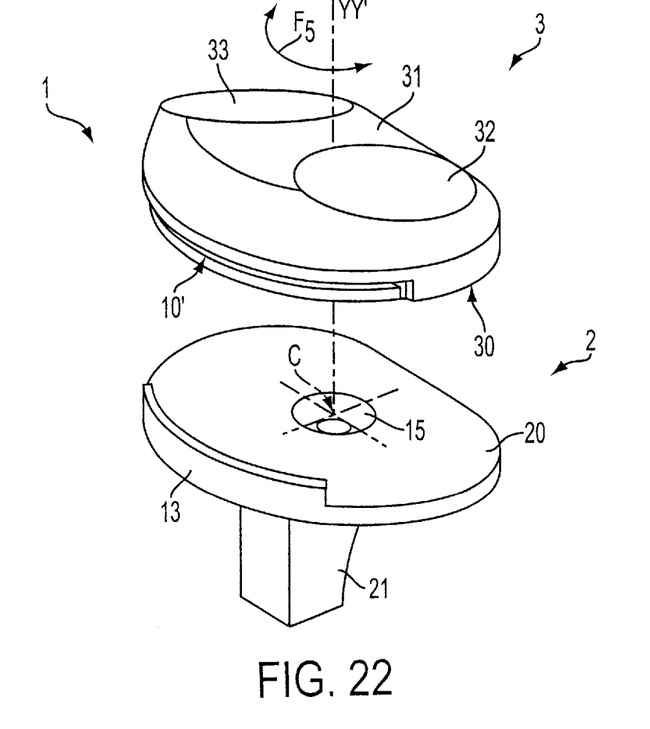
FIGS. 22 to 24 are views depicting other alternative forms of the knee prosthesis according to the present invention.
Figure 23:
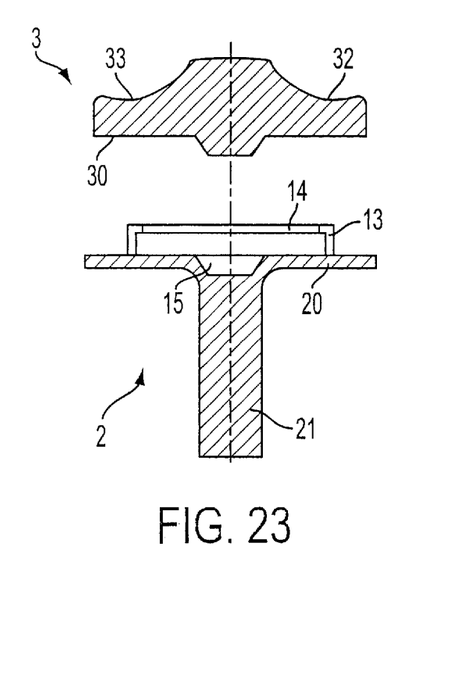
Figure 24:
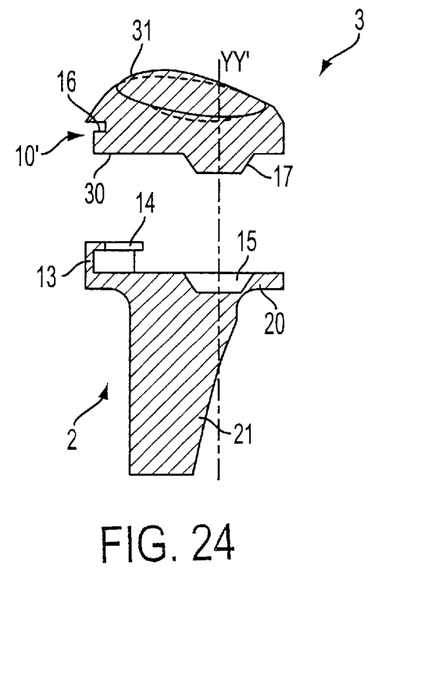

In FIGS. 22 to 24 the knee prosthesis 1 comprises the metal base 2, the horizontal disk 20 of which has, on its external periphery, an upstand 13 in the shape of an arc of a circle integral with a flange 14 directed toward the tibia bone vertical axis YY'.

The horizontal disk 20 is pierced at the center of rotation C of the upstand 13 with a dish-shaped housing 15 which constitutes a guide mechanism that is in addition to the guide mechanism formed by the upstand 13. This upstand, which is in the shape of an arc of a circle or curved, is positioned in the anterior part of the metal base 2 and oriented in a substantially medio-lateral direction.

The upstand 13 and the housing 15 may comprise a center of rotation C which is offset from the tibia bone vertical axis YY'.

On its external periphery and between the faces 30 and 31, the tibia plate 3 has a recess 10' in which there is formed a horizontal slot 16 intended to receive the flange 14 of the upstand 13 as the plate 3 slides in rotation over the metal base 2.

The lower face 30 is integral with a stub 17 with a conical tapering profile capable of engaging with the housing 15 formed in the horizontal disk 20 of the metal base 2.

The upstand 13 equipped with its flange 14, the housing 15, the recess 10' and its slot 16, and the stub 17 constitute the mechanism of guiding the tibia plate 3 over the metal base 2 as the plate slides in rotation in the direction of the arrow F5.

Figures 25, 26:
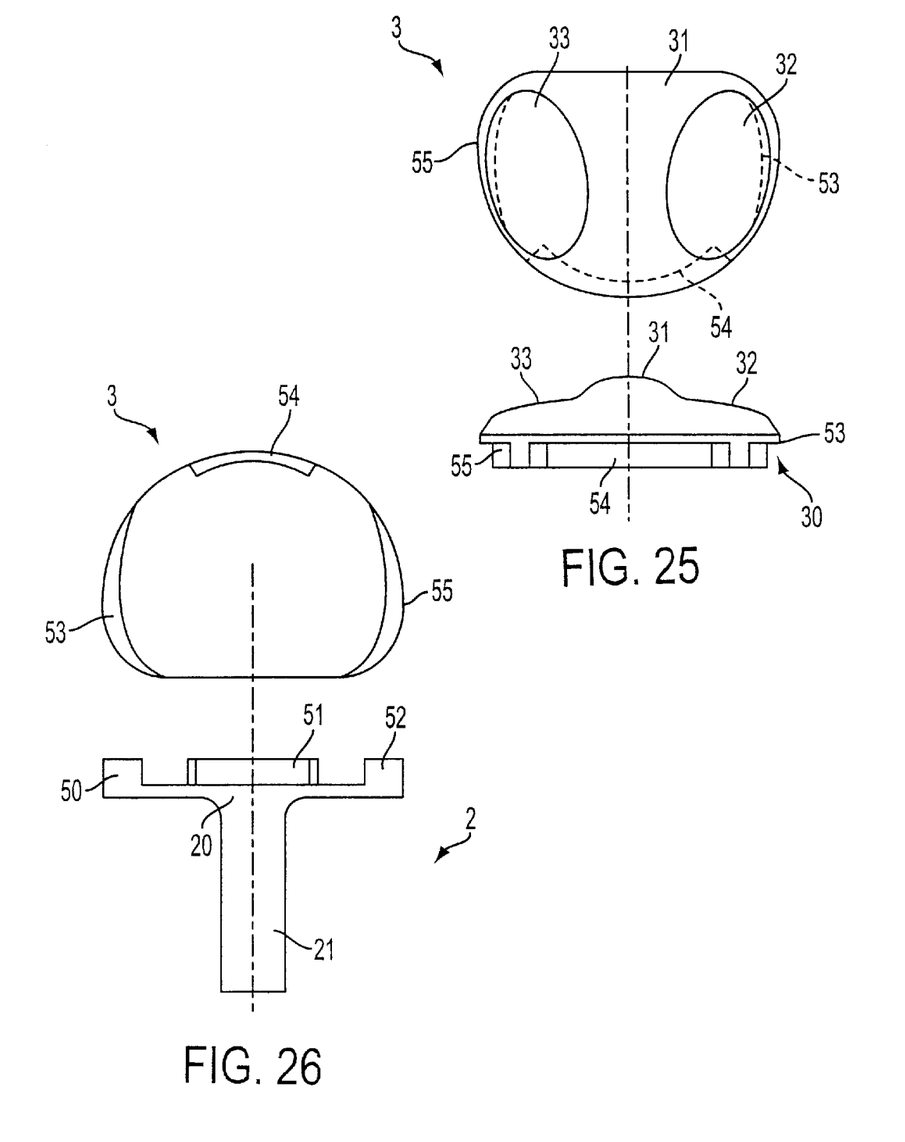
FIGS. 25 and 26 are views illustrating guide mechanism set out at the periphery of the metal base and of the tibia plate of the knee prosthesis.

In FIGS. 25 and 26, the metal base 2 of the knee prosthesis 1 comprises, on its horizontal disk 20, three peripheral upstands 50, 51 and 52 extending vertically above the said horizontal disk 20.

The tibia plate 3 comprises, on its external periphery, three peripheral recesses 53, 54 and 55 which are intended to receive the upstands 50, 51 and 52 respectively to allow the plate to be guided as it slides in rotation about the center of rotation of the upstands, which is identical for all three.

The upstand 51, which is the shape of an arc of a circle or curved, is positioned in the anterior part of the metal base 2 and oriented in a substantially medio-lateral direction.

The upstands 50, 52 in the shape of an arc of a circle constitute guide mechanism which are in addition to the guide mechanism formed by the upstand 51. The upstands 50, 52 are positioned near the center of rotation C of the tibia plate 3 on the metal base 2.

Figure 27:
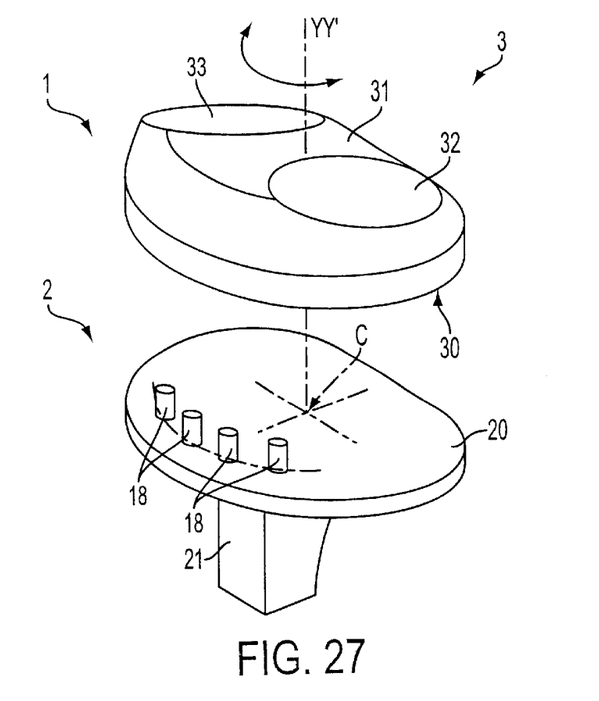
FIGS. 27 to 29 are views showing guide mechanism utilizing of at least two vertical pegs integral with the metal base and which engage with a housing formed in the tibia plate.
Figure 28:
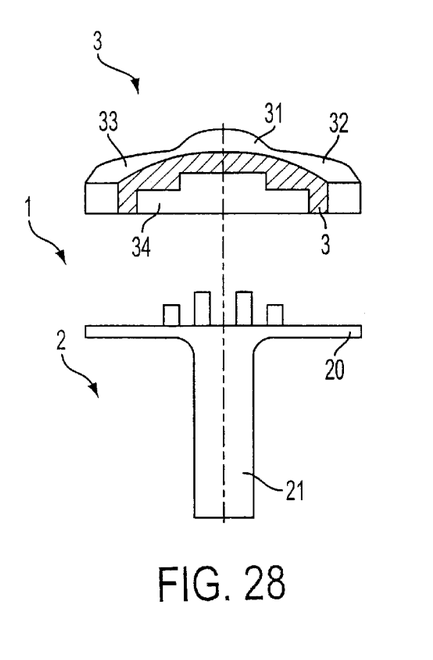
Figure 29:
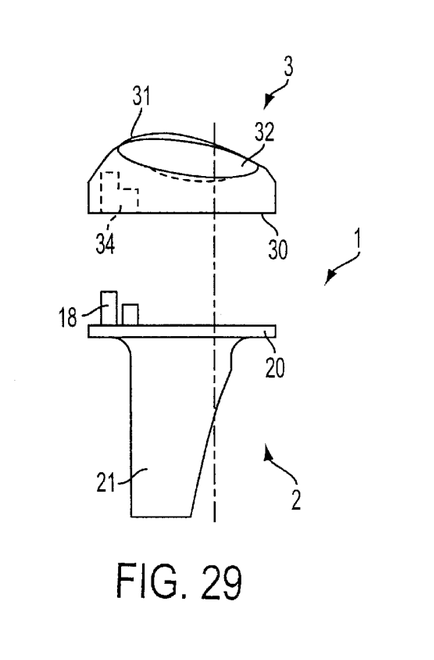

In FIGS. 27 to 29, the metal base 2 of the knee prosthesis 1 comprises, on its horizontal disk 20, vertical pegs 18 set out in an arc of a circle about a center of rotation C which may be either borne by or offset from the tibia bone vertical axis YY'.

The pegs 18 set out in an arc of a circle are positioned in the anterior part of the metal base 2 and oriented in a substantially medio-lateral direction.

In this example, the tibia plate 3 is identical to the one described in FIGS. 1 to 3, that is to say that its lower face 30 has a housing 34 intended to receive the pegs 18 for guiding the plate as it slides in rotation with respect to the metal base 2.

It can be seen that in each example described hereinabove it is possible, as the case may be, for the center of rotation of the upstands or of the pegs either to be offset or not to be offset in order to determine a particular rotational sliding of the tibia plate 3 with respect to the metal base 2.

Note too that in each example described hereinabove, cutouts 4 and 38 may or may not be provided for the passage of the posterior cruciate ligament.

Furthermore, it can be seen that the guide mechanism in each example described hereinabove are positioned a certain distance away from the center of rotation C, C'.

It will be observed that the short height of the upstand or of the pegs, and its anterior position on the metal base 2 allows the plastic plate 3 to be fitted onto the base easily using a strictly anterior approach, the plate requiring upward clearance only by the height of the upstand or of the pegs as shown in FIG. 18.

It will furthermore be observed that the plastic plate 3 cannot slide in rotation over the metal base 2 except within the limits set by the difference in dimensions between the housing and the corresponding upstand or peg, and this prevents any undesired excess movement.

This being so, it will be readily understood that a plastic plate 3 can be obtained in which the dimensions of the housing are identical to those of the upstand or of the corresponding pegs, so as to prevent any travel of the plate over the metal base 2. This allows the surgeon, according to the particular surgical case, to return to a knee prosthesis system with plastic plate which is fixed to the metal base 2, without having to change the latter.

What is claimed is:

1. Knee prosthesis comprising:
   a metal base secured to an anchoring rod for fixing it into a tibia of a patient;
   a plastic tibia plate freely slidable over said base;
   the metal base and the tibia plate being equipped with a guide mechanism defining a center of rotation offset from that of a tibia bone axis, so as to allow the plate to slide in rotation over said base;
   said guide mechanism being positioned a given distance from the center of rotation;
   said metal base comprising an upstand in the shape of an arc of a circle having a central part secured to lateral edges which are shorter than said central part;
   said tibia plate comprising, on a lower face thereof, a housing in the shape of an arc of a circle.

2. Knee prosthesis according to claim 1, wherein said upstand is secured to the metal base, said housing having the same radius of curvature as the tibia plate to allow the latter to slide in rotation about a center of rotation of said upstand.

3. Knee prosthesis according to claim 2, wherein the upstand has a center of rotation which is borne by a tibia bone vertical axis, while said upstand is a given distance from its center of rotation.

4. Knee prosthesis according to claim 2, wherein the upstand has a center of rotation which is offset from a tibia bone vertical axis, while said upstand is a given distance from its center of rotation.

5. Knee prosthesis according to claim 1, wherein the metal base comprises said upstand, said upstand being of a first size, said upstand engaging with a housing of the tibia plate, said housing being of a second size, to permit said tibia plate to slide in rotation over the metal base only within the limit set by the difference in size between the said upstand and said housing.

6. Knee prosthesis according to claim 1, wherein the guide mechanism has a height and is positioned anteriorly on the metal base so as to permit the tibia plate to be mounted on said base via a strictly anterior approach, said plate requiring upward clearances only to the extent of the height of said guide mechanism.

* * * * *